(12) United States Patent
Brimhall et al.

(10) Patent No.: US 6,719,727 B2
(45) Date of Patent: *Apr. 13, 2004

(54) CATHETER HAVING A WING WITH A STIFFENING MEMBER THEREIN

(75) Inventors: Greg L. Brimhall, West Jordan, UT (US); Stephen L. Thoresen, Orem, UT (US)

(73) Assignee: Becton Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/865,297

(22) Filed: May 25, 2001

(65) Prior Publication Data

US 2002/0177816 A1 Nov. 28, 2002

(51) Int. Cl.[7] ................... A61M 5/178; A61M 5/32
(52) U.S. Cl. ..................... 604/177; 604/165.03
(58) Field of Search ................ 604/177, 179, 604/165.01, 165.07, 165.03, 174, 164.04, 180, 161, 165.02, 178, 533, 538, 539, 535, 171, 175, 176, 523; 128/DIG. 26

(56) References Cited

U.S. PATENT DOCUMENTS

| 3,651,807 | A | * | 3/1972 | Huggins | 604/161 |
| 4,324,236 | A | * | 4/1982 | Gordon et al. | 128/214 |
| 4,650,473 | A | | 3/1987 | Bartholomew et al. | 604/174 |
| 4,698,057 | A | | 10/1987 | Joishy | 604/176 |
| 4,834,708 | A | * | 5/1989 | Pillari | 604/165.04 |
| 4,863,432 | A | * | 9/1989 | Kvalo | 604/177 |
| 4,969,876 | A | | 11/1990 | Patterson | 604/171 |
| 5,147,319 | A | * | 9/1992 | Ishikawa et al. | 604/174 |
| 5,304,144 | A | | 4/1994 | Brimhall | 604/177 |
| 5,322,512 | A | * | 6/1994 | Mohiuddin | 604/160 |
| 5,385,554 | A | * | 1/1995 | Brimhall | 604/168 |
| 5,807,342 | A | * | 9/1998 | Musgrave et al. | 604/177 |
| 6,063,037 | A | * | 5/2000 | Mittermeier et al. | 600/567 |

FOREIGN PATENT DOCUMENTS

| EP | 0 732 120 A1 | 9/1996 |
| EP | 0 792 658 A2 | 9/1997 |

* cited by examiner

Primary Examiner—Brian L. Casler
Assistant Examiner—Matthew F Desanto
(74) Attorney, Agent, or Firm—James J. Murtha

(57) ABSTRACT

A catheter assembly is disclosed having wings extending from the catheter adapter wherein each of the wings includes a stiffening member located therein. Each of the stiffening members may also define a means for maintaining the position of the stiffening members during the molding process to ensure that the stiffening member is properly located in the wing.

19 Claims, 13 Drawing Sheets

CATHETER HAVING A WING WITH A STIFFENING MEMBER THEREIN

BACKGROUND OF THE INVENTION

The subject invention relates to an intravascular ("IV") medical device. More specifically, this invention relates to an IV catheter that is adapted to be affixed to the patient's skin. Even more specifically this invention relates to an IV catheter having wings that are each formed with a stiffening member therein. In addition, this invention relates to a catheter wing and stiffening member configuration and method for forming the catheter wing and stiffening member that maintains the ornamental and functional features of the wing and stiffening member. The invention results in a catheter wing that facilitates the introduction of the catheter into a patient's vasculature yet maximizes patient comfort when the wing is affixed to the patient's skin.

In order properly to place an IV catheter into a patient, the catheter is typically mounted over an introducer needle having a sharp distal tip. At least the distal portion of the catheter tightly engages the outer surface of the needle to prevent peelback of the catheter and thus facilitates insertion of the catheter into the blood vessel. The distal tip of the needle preferably extends beyond the distal tip of the catheter with the bevel of the needle facing up away from the patient's skin.

The catheter and introducer needle assembly is inserted at a shallow angle through the patient's skin into a blood vessel. Some catheters include wings, which may be used to facilitate this venipuncture and to facilitate securing the catheter to the patient as discussed below. The wings extend from either side of the catheter or catheter hub and aid the clinician to precisely manipulate and control the position of the catheter during venipuncture. In some cases the wings may be folded together like butterfly wings. In order to verify proper placement of the catheter in the blood vessel, the clinician confirms that there is flashback of blood in a flashback chamber. The flashback chamber is typically formed as part of the needle hub. Once proper placement of the catheter into the blood vessel is confirmed, the clinician applies pressure to the blood vessel by pressing down on the patient's skin over the blood vessel distal of the needle and the catheter. This finger pressure occludes or at least minimizes further blood flow through the needle and the catheter. The clinician then withdraws the needle, leaving the catheter in place for use in accordance with standard medical technique.

Peripheral IV catheters are short, and are typically on the order of between about ¾ of an inch and about 3 inches long. Because of the shortness of the catheter, it is typically taped or sutured to the patient's skin. Taping or suturing the catheter to the patient's skin minimizes the possibility that the catheter will become dislodged from the patient's vein if the patient moves or a clinician manipulates the catheter to connect or disconnect an IV line or other medical device. To facilitate this taping or suturing, some catheters include wings extending about 180 degrees apart from either side of the catheter hub. In some devices, the ends of the wings include suture holes that allow the clinician to sew the catheter directly to the patient's skin.

In order to maximize patient comfort, these wings are typically formed from a soft and flexible material such as silicone. This type of material is comfortable to the touch and has no hard portions that could dig into the patient's skin causing abrasions or pressure points. However, materials having the desired softness for maximizing patient comfort may not have sufficient rigidity to allow the clinician to precisely manipulate and control the position of the catheter during venipuncture. Such softness and flexibility could allow the wings to flex or fold so that when the clinician grasps the catheter by the wings, the catheter may not be properly aligned with the longitudinal and radial axis of the wings. This makes it difficult for a clinician to use the wings to control the location of the catheter with respect to the wing and the venipuncture site. To date, an appropriate balance between soft, flexible wings that maximize patient comfort when the catheter is affixed to the patient's skin and hard, stiff wings that maximize the ability of the clinician to precisely control the catheter during venipuncture has not been found in available devices.

SUMMARY OF THE INVENTION

It is therefore an object of this invention to provide a catheter that maximizes patient comfort when the catheter is affixed to the patient's skin and that also maximizes the ability of the clinician to precisely control the catheter during venipuncture.

It is another object of this invention to provide a catheter wing configuration that balances the functional and ornamental characteristics of wings formed from soft, flexible material and wings formed from hard, rigid material.

It is yet another object of this invention to provide a method for forming a catheter wing configuration that achieves the objects of this invention.

This invention is particularly useful when applied to a catheter, especially a catheter having an integrated extension tube extending from the catheter adapter (an "integrated catheter"), although it is to be understood that this invention is applicable to other medical devices that require wings to facilitate both affixing the device to the patient's skin or precisely manipulating the medical device.

The catheter is coaxially disposed over the introducer needle with the distal portion of the catheter tightly engaging the outer surface of the introducer needle. This prevents peelback of the catheter and facilitates insertion of the catheter into the patient's blood vessel. Prior to use, the catheter is located about the introducer needle so that the sharp distal tip of the introducer needle is distal of the distal end of the catheter. The proximal end of the catheter is connected to a catheter adapter. A pair of wings extends about 180 degrees apart from either side of the catheter adapter. The ends of each wing may define a suture hole that allows a clinician to sew the wing, and thus the catheter, directly to the skin of the patient.

The introducer needle has a sharp distal tip and a proximal end connected to the distal end of a needle hub and preferably includes at least one notch, i.e. a hole or opening in the sidewall, therein in communication with the needle lumen. The notch is formed in the introducer needle such that blood can flow into the open distal end of the introducer needle, through the lumen in the introducer needle and through the notch outside the introducer needle into the catheter lumen. Thereafter, the blood can flow through the annular space between the outside of the introducer needle and the inside of the catheter and catheter adapter and then through the side arm and extension tube that extends from the catheter adapter. Preferably, the catheter, catheter adapter and the extension tube are transparent or at least translucent. In this way, the clinician can immediately and easily visualize flashback of blood through these parts of the catheter assembly when the introducer needle has been inserted into a patient's blood vessel.

If desired, a needle shield movably disposed about the introducer needle and located distally of the needle hub is defined by a housing having an internal cavity through which the introducer needle extends. A lock associated with the needle shield prevents unwanted distal movement of the introducer needle once the introducer needle has been proximally withdrawn into the needle shield. Also associated with the needle shield is a means for preventing unwanted proximal movement of the introducer needle once the sharp distal tip of the introducer needle has been proximally withdrawn into the needle shield.

The catheter wing includes a stiffening member disposed therein. Preferably the wing is formed from a thermoplastic elastomer. The stiffening member may be formed from the same material used to form the catheter adapter and is preferably a polycarbonate material or polyethylene phthalate glycol (PETG). The soft, flexible material of the wing is comfortable to the touch and covers any hard edges or other surfaces to prevent skin abrasion or pressure points on the patient's skin when the wing is taped to or sutured onto the patient's skin. The hard, rigid material of the stiffening member provides rigidity to the wing to allow the clinician to precisely control the position and movement of the catheter.

Suture holes may be formed at the ends of each wing. These suture holes provide a dual function. As is standard with all suture holes, the suture holes of this invention provide a mechanism that allows the clinician to sew the wings, and thus the catheter, directly to the patient's skin, which fixes the catheter in place. In addition, the suture holes provide a mechanism to hold the stiffening members in place when the wings are formed. The wings are formed by injection molding the wing material over the stiffening members. Without some fixation device to hold the stiffening members in place, the high pressure used during the injection molding process will cause the stiffening members to become dislodged with the result that they will not be located in the optimum position within the wing. With the suture holes of this invention, pins can be used during the molding process to precisely locate the stiffening members with respect to the wing to be overmolded thereon. This prevents the stiffening members from becoming dislodged from their location even under the high pressure of the injection molding process. Alternatively, the ends of the stiffening members could be formed with upwardly and downwardly extending integral pins. These pins in turn would sit in appropriate holes formed in the mold to precisely locate the stiffening members with respect to the wing to be overmolded thereon.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
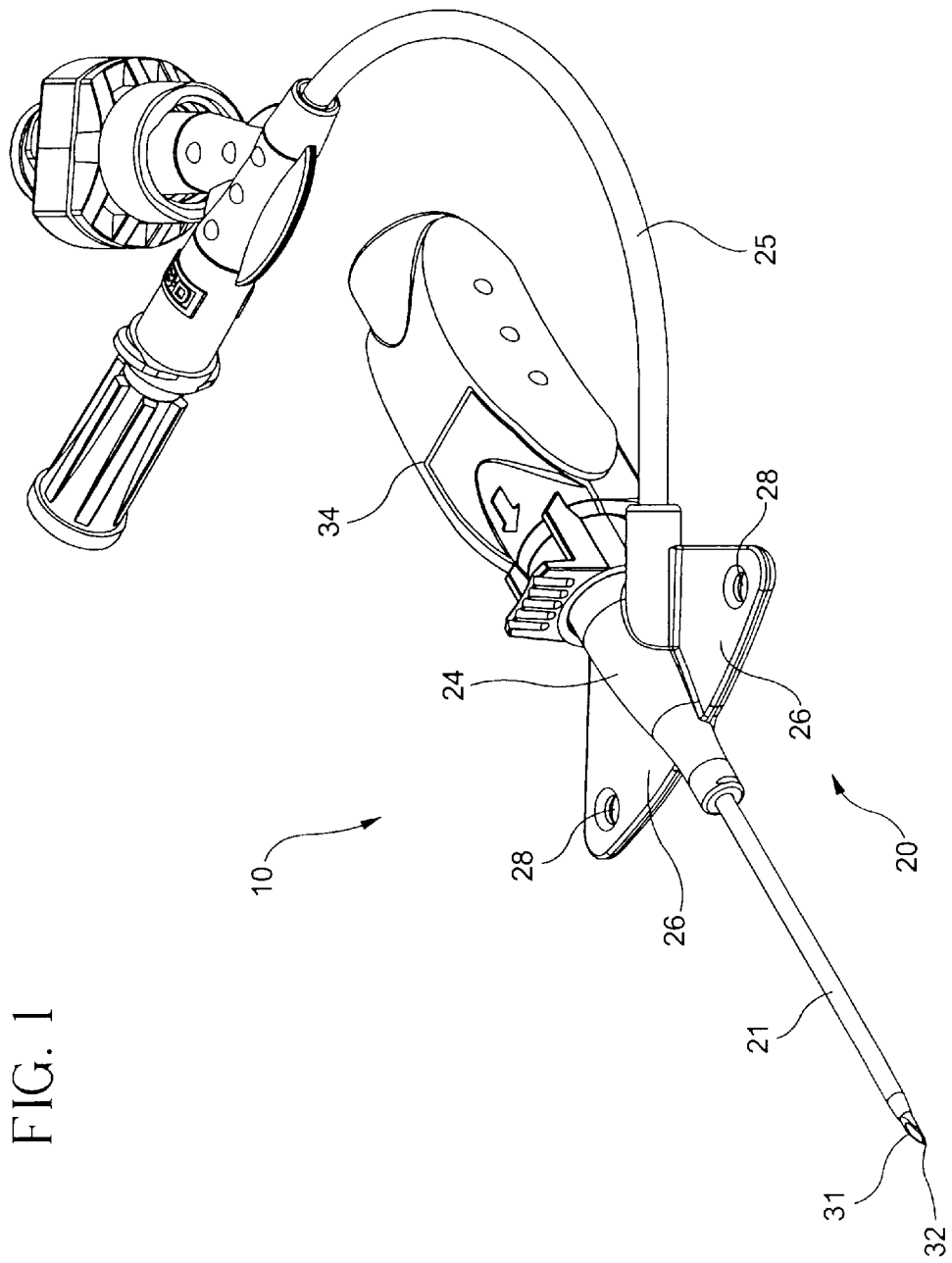
FIG. 1 is a perspective view of an integrated catheter with an introducer needle assembly that incorporates the wing and one embodiment of the stiffening member of this invention ready for use.
Figure 2:
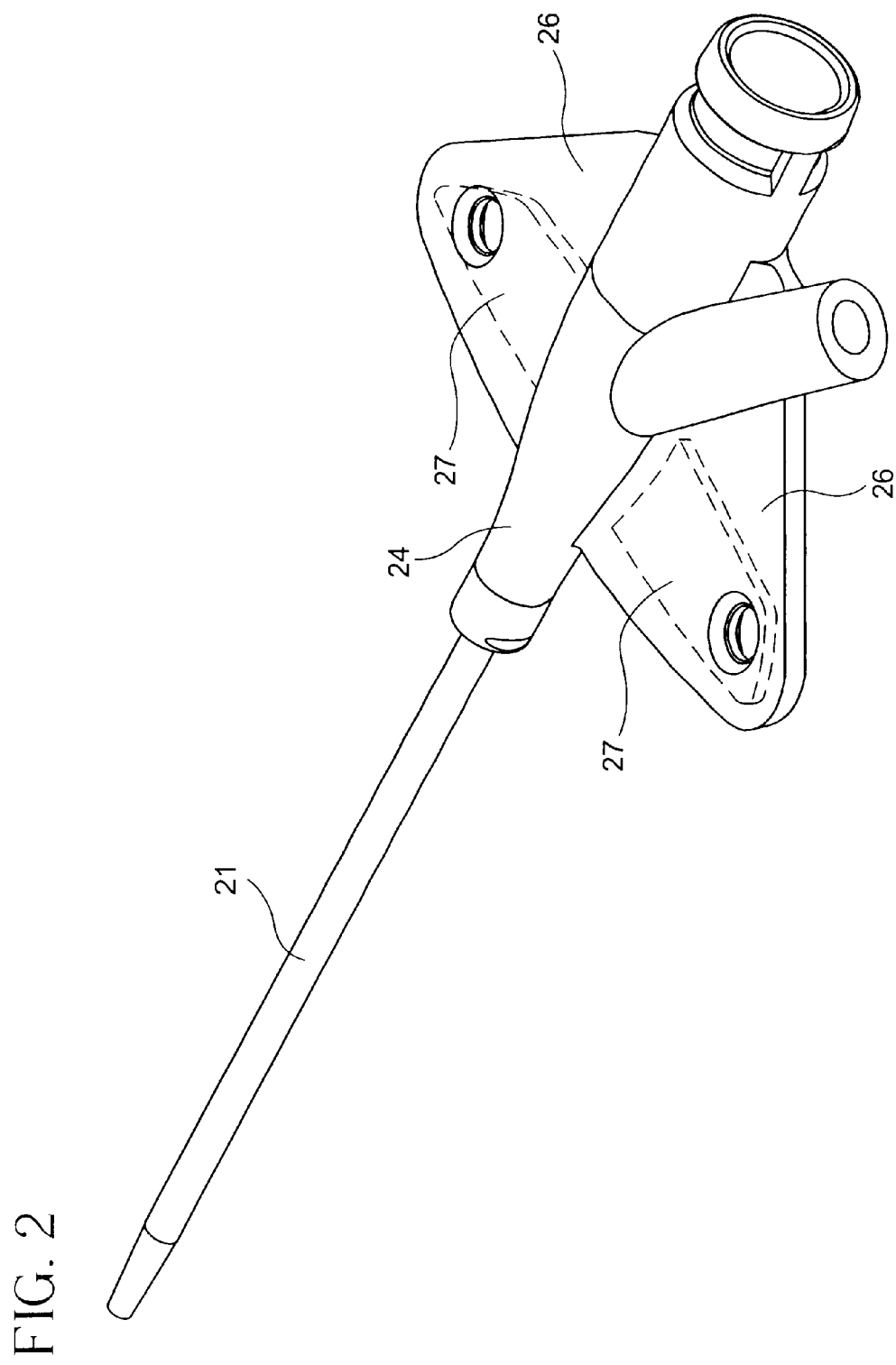
FIG. 2 is a top perspective view of the integrated catheter shown in FIG. 1 with the wings and stiffening member in phantom but without the extension tube attached to the side arm or the introducer needle assembly.
Figure 3:
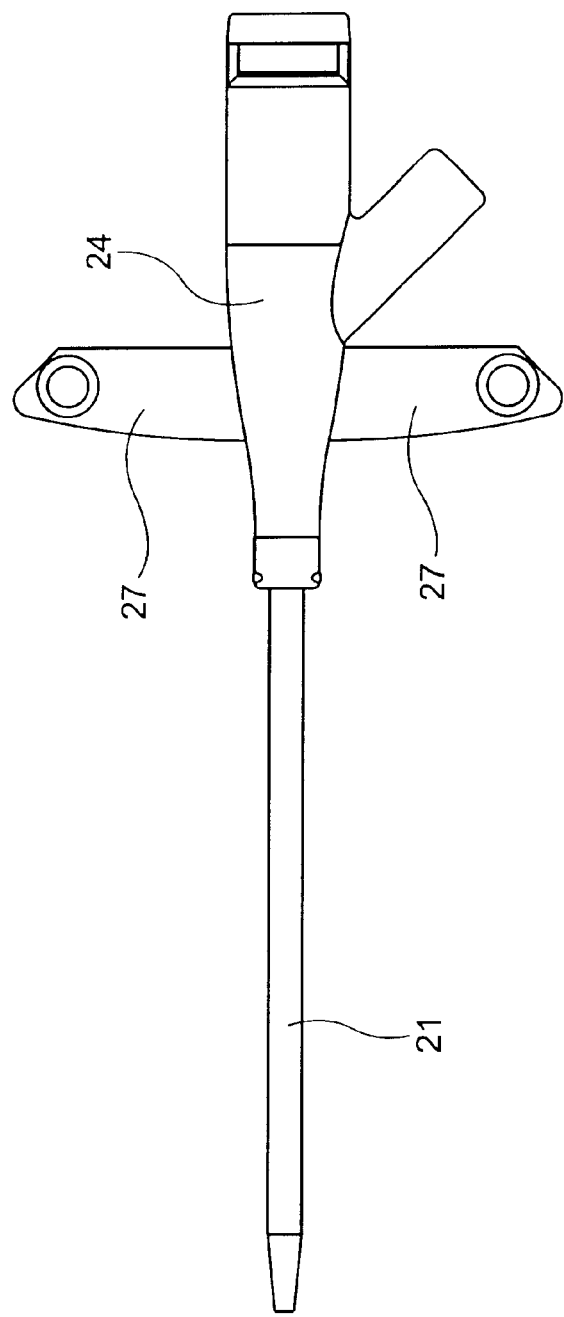
FIG. 3 is a top plan view of a partially assembled integrated catheter of FIG. 2 showing the catheter, the catheter adapter, the side arm and the stiffening members prior to the wings being overmolded thereon.
Figure 4:
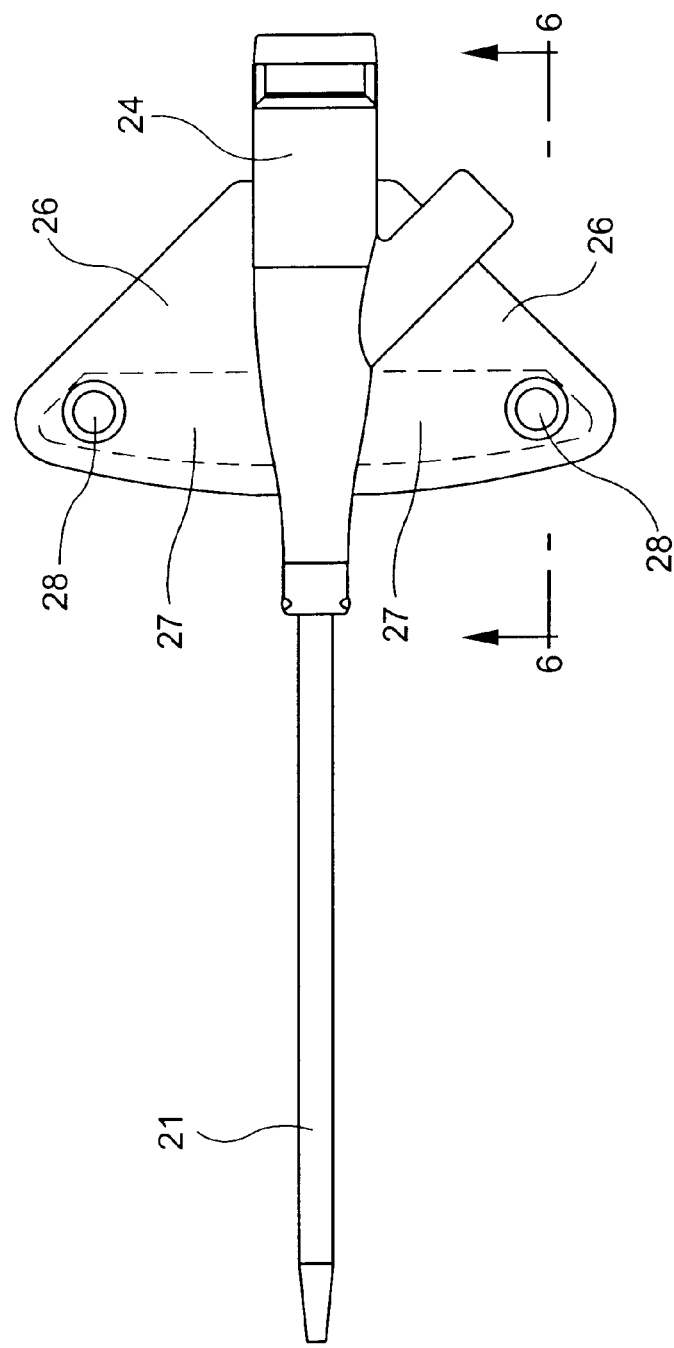
FIG. 4 is a top plan view similar to FIG. 3 but with the wings overmolded on the stiffening members, which are shown in phantom.
Figure 5:
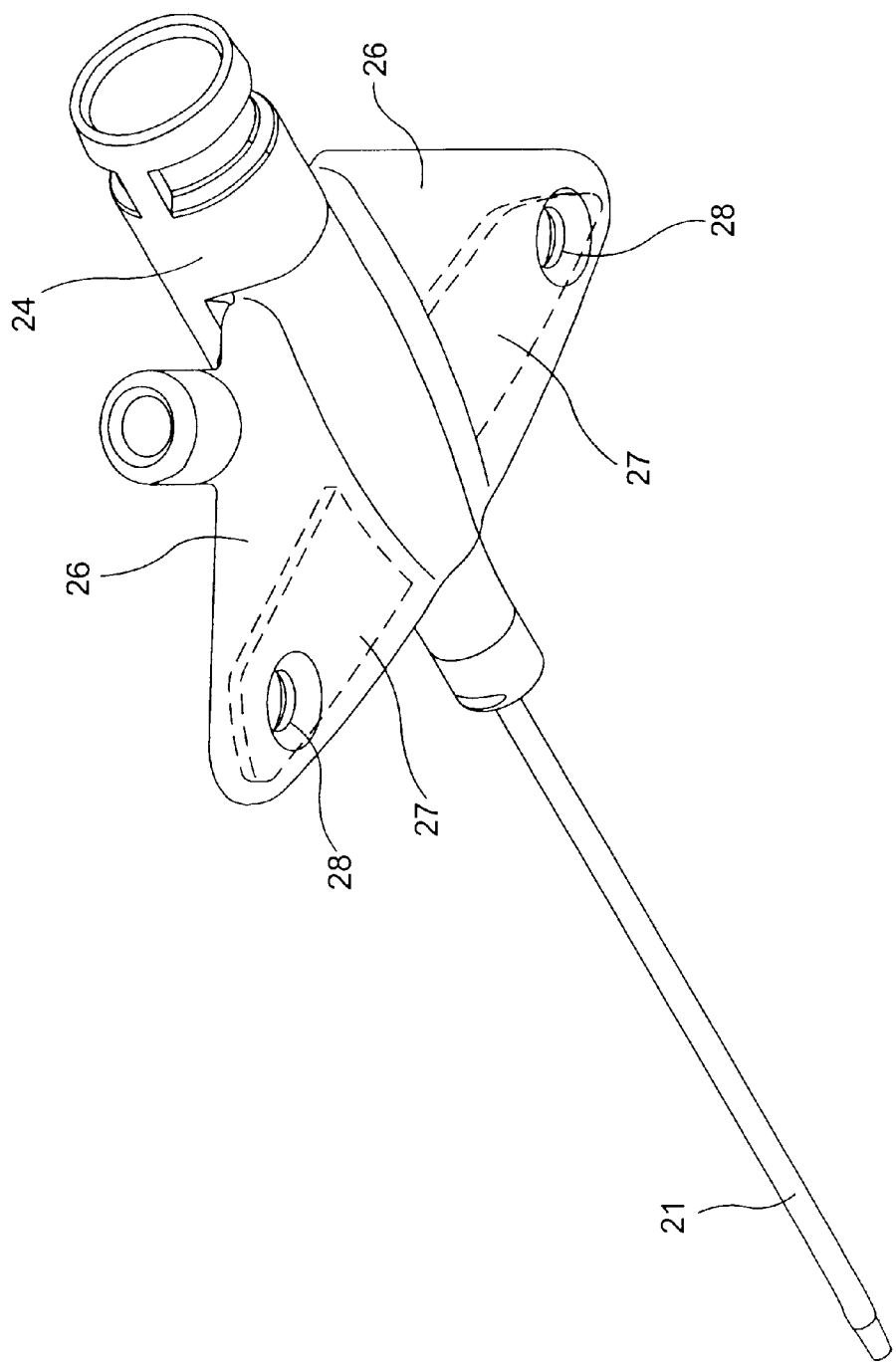
FIG. 5 is a bottom perspective view of the integrated catheter shown in FIG. 2 with the wings and stiffening member in phantom but without the extension tube attached to the side arm.
Figure 6:
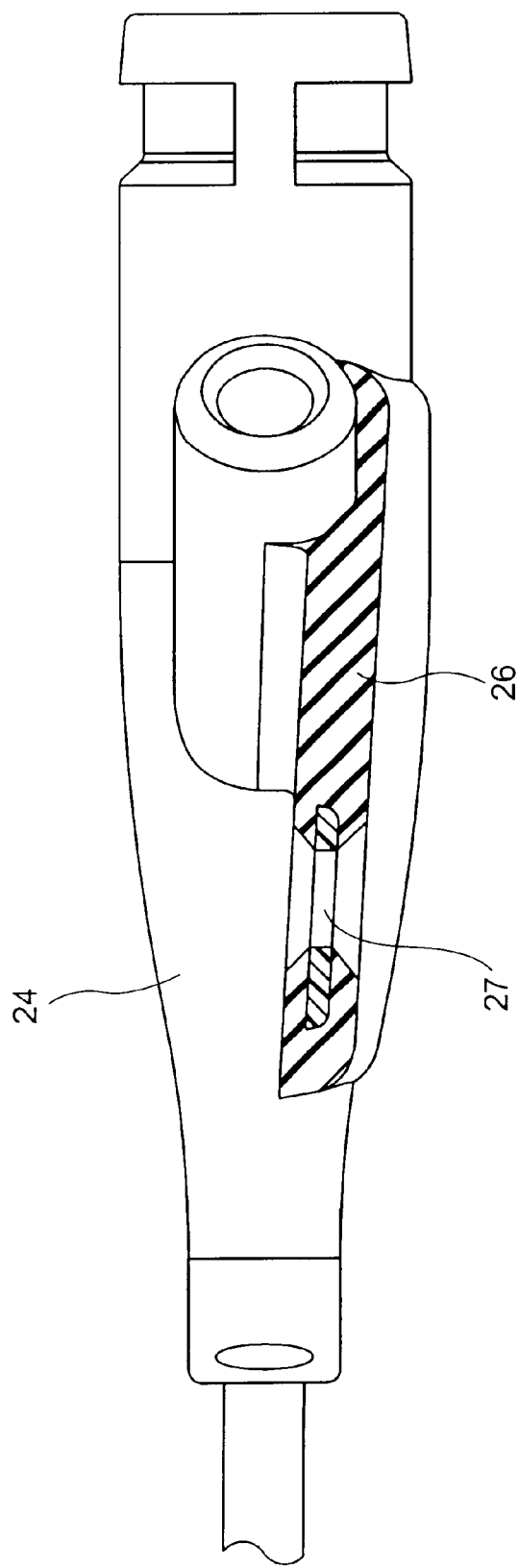
FIG. 6 is a side elevation view, partially in cross section, of the integrated catheter taken along line 6—6 of FIG. 4.

As used herein, the term "proximal" refers to a location with respect to the device that, during normal use, is closest to the clinician and farthest from the patient. Conversely, the term "distal" refers to a location with respect to the device that, during normal use, is farthest from the clinician and closest to the patient. As used herein, the term "top", "up" or "upwardly" refers to a location with respect to the device that, during normal use, is radially away from the longitudinal axis of the device and away from the patient's skin. Conversely, as used herein, the term "bottom", "down" or "downwardly" refers to a location with respect to the device that, during normal use, is radially away from the longitudinal axis of the device and toward the patient's skin. As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

This invention is described herein using like reference numbers for like elements in the different embodiments. Although this invention is described herein in connection with a peripheral IV catheter having an integrated extension tube (an "integrated catheter"), it is to be understood that this invention is applicable to other catheters such as standard peripheral IV catheters. In addition, it is to be understood that this invention is applicable to catheter introducers and guidewire introducers and other medical devices that are designed to be inserted into a patient's vasculature using a standard over the needle insertion technique. Finally, while this invention is satisfied by embodiments in many different forms, there are shown in the drawings and herein described in detail, preferred embodiments of the invention with the scope of the invention measured by the appended claims.

An integrated catheter and introducer needle assembly including the wings and one embodiment of the stiffening members of this invention is shown generally at 10 in FIG. 1. Catheter assembly 20 includes a catheter 21 that has a proximal end, a distal end and a catheter adapter 24 affixed to the proximal end of catheter 21. Suitable materials for catheter 21 include, but are not limited to, thermoplastic resins such as fluorinated ethylene propylene (FEP), polytetrafluoroethylene (PTFE), polyurethane and the like. Preferably, catheter 21 is formed from a thermoplastic hydrophilic polyurethane that softens with exposure to physiological conditions present in the patient's body. In addition, the material used to form catheter 21 is preferably transparent or at least translucent. In addition, if desired, catheter 21 can be formed so that it is partially transparent or translucent such as where catheter 21 is formed from stripes of transparent or translucent material. This allows the clinician to see blood flashback in the annular space between the introducer needle 31 and catheter 21 where introducer needle 31 includes a notch, i.e. a hole or opening in the sidewall, adjacent to its distal end to allow such blood flow. Suitable materials for catheter adapter 24 include, but are not limited to, thermoplastic polymeric resins such as polycarbonate, polystyrene, polypropylene, poly ethylene phthalate glycol (PETG) and the like. Preferably the material used to form catheter adapter 24 is transparent or at least translucent to allow the clinician to view blood flashback therein. An integrated extension tube 25 extends from catheter adapter 24 and may include a hub or some type of fluid access device at its proximal end. See FIG. 1. Extension tube 25 may also be translucent to allow the clinician to view flashback of blood therein to confirm successful venipuncture. Details of such an integrated catheter are described generally in U.S. Pat. No. 5,697,914.

Catheter adapter 24 includes a pair of wings 26 formed thereon. Each wing 26 includes a stiffening member 27 disposed therein. Wings 26 are preferably formed from a thermoplastic elastomer such as those materials sold by Kraiburg under the Thermolast K TF7MAA designation or by Multibase under the Multi-Flex TEA 1004 designation. Preferably this material should have a hardness in the range of between 60 Shore A and 85 Shore A, although a hardness outside of this range would also be appropriate. The soft, flexible material used to form wings 26 is comfortable to the touch and covers the hard edges and other surfaces of stiffening members 27 to prevent skin abrasion or pressure points on the patient's skin when catheter adapter 24 is taped to or sutured onto the patient's skin. Preferably, stiffening members 27 should be more rigid than wings 26.

Wings 26 should be large enough to provide patient comfort and to allow it to be effectively secured to the patient. Preferably, wings 26 are located adjacent to the bottom of catheter adapter 24. This ensures that the clinician will have a clear view of the top of catheter adapter 24 and can thus immediately and easily see blood flashback in catheter 21 and catheter adapter 24, if they are formed from translucent material, to confirm successful venipuncture.

The hard, rigid material of stiffening members 27 provides rigidity to wings 26 to allow the clinician to precisely control the position and movement of catheter assembly 20. Stiffening members 27 should be large enough to provide the desired rigidity of wings 26 but should not be so large as to adversely impact the softness of wings 26. Preferably, each stiffening member 27 has a longitudinal dimension, i.e. measured from its proximal end to its distal end that is larger than its thickness, i.e. the dimension measured from its top and bottom. For example, each stiffening member preferably has a longitudinal dimension of about 0.175 inches and a thickness of about 0.015 inches. In addition, the added rigidity provided by stiffening members 27 allows the clinician to shape wings 26 to more closely match the contour of the patient's skin and thus enhance patient comfort.

Suture holes 28 may be formed at the ends of each wing 26 and extend through the soft, flexible material forming wings 26 as well as stiffening members 27. Suture holes 28 provide a dual function. As is standard with all suture holes, suture holes 28 provide a mechanism that allows the clinician to sew wings 26, and thus catheter assembly 20, directly to the patient's skin, which fixes catheter assembly 20 in place. In addition, by forming suture holes 28 so they extend through stiffening members 27, suture holes 28 provide a mechanism to hold stiffening members 27 in place when wings 26 are formed.

Figure 7:
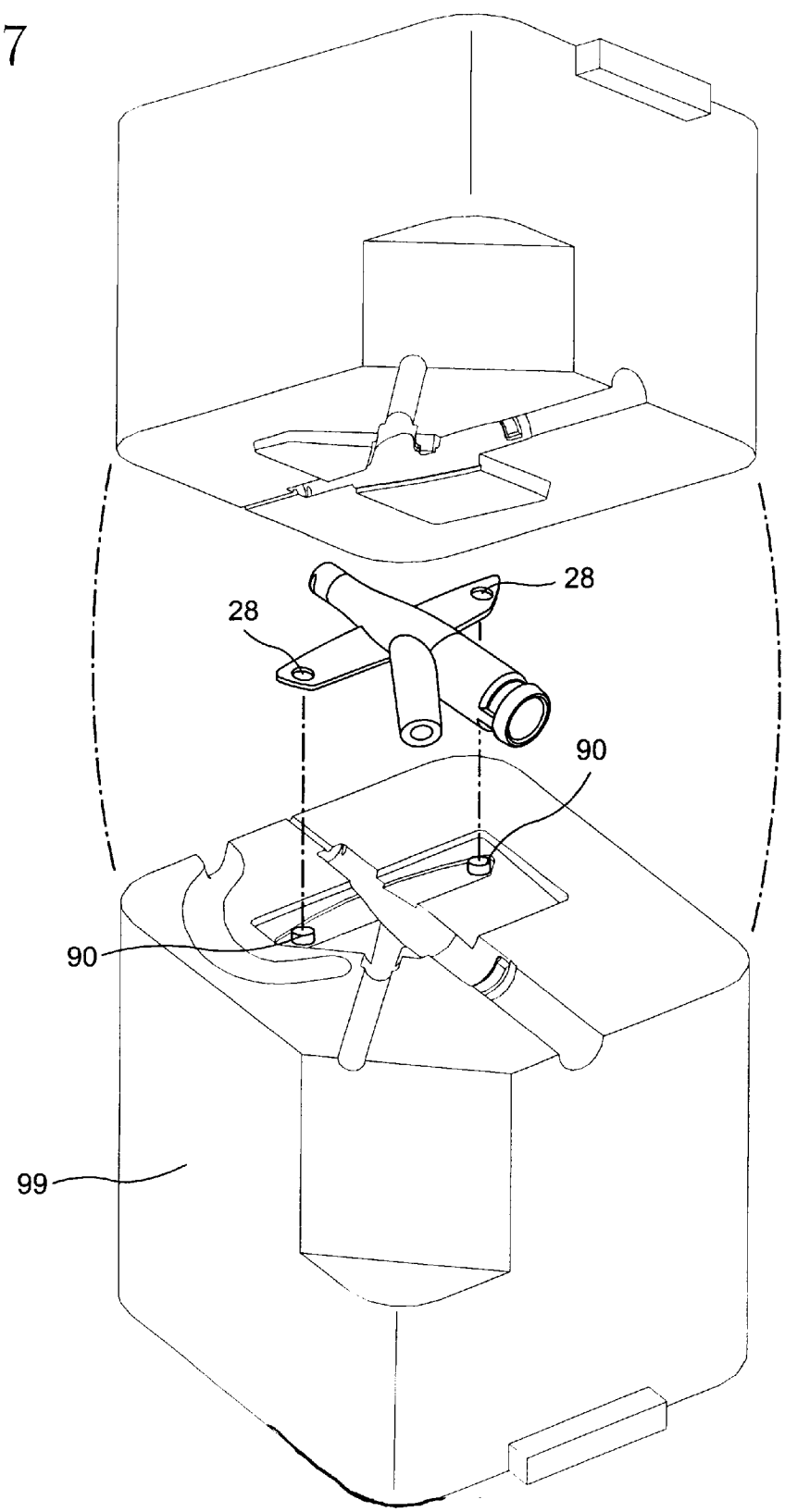
FIGS. 7 and 8 are schematic diagrams of the manufacturing process for the wings and stiffening member of the integrated catheter of FIG. 2.
Figure 8:
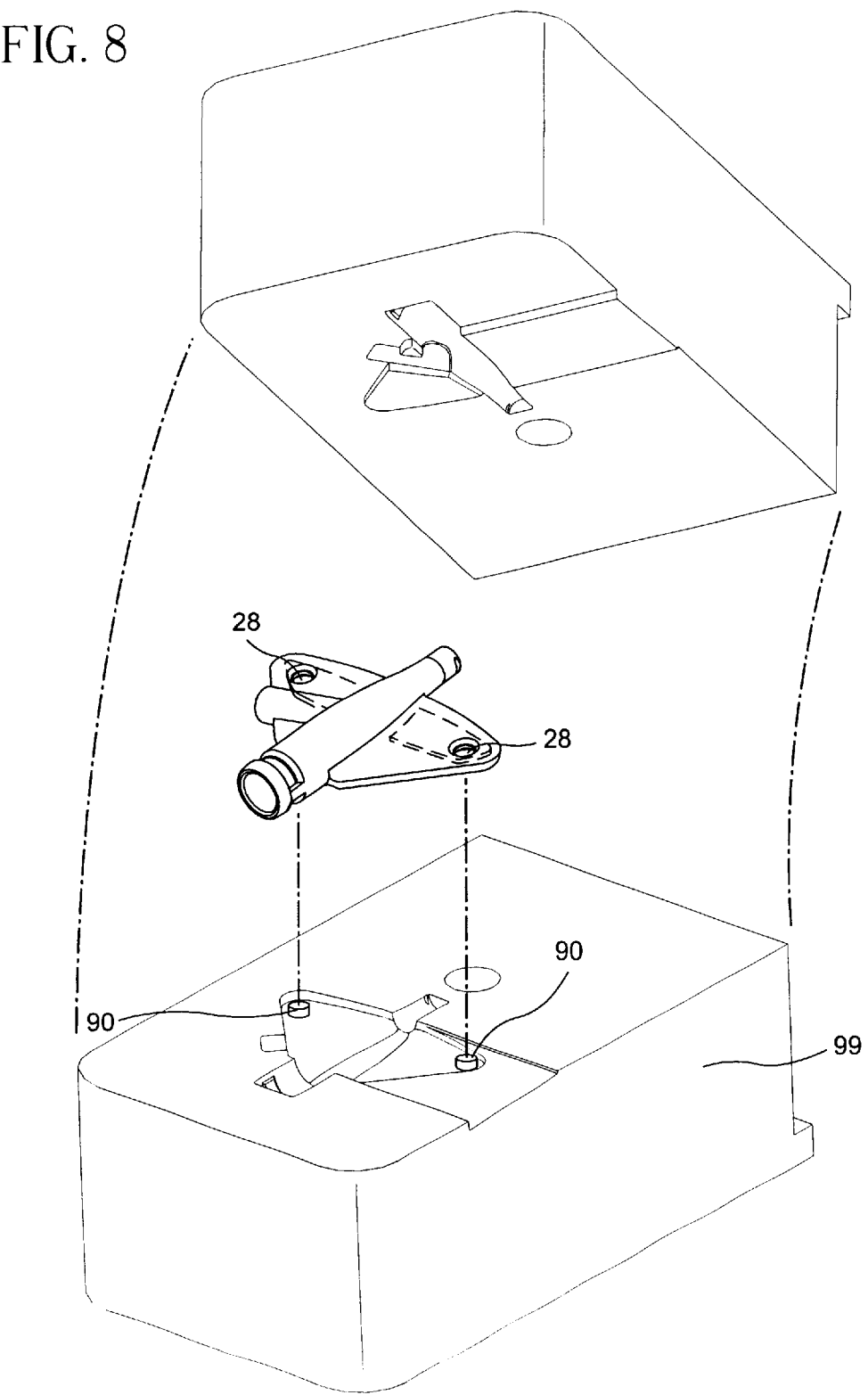

Wings 26 are formed by injection molding the wing material over stiffening members 27. Without some fixation device to hold stiffening members 27 in place, the high pressure used during the injection molding process will cause stiffening members 27 to become dislodged or mis-oriented with the result that they could be moved out of the optimum position within wings 26 and could in fact extend out of the wings. By forming suture holes 28 of this invention so they extend through stiffening members 27, pins 90 formed in the mold 99 can be used during the molding process to precisely locate each stiffening member 27 with respect to each wing 26 to be overmolded thereon. Pins 90 extend through the holes formed in the end of each stiffening member 27 to fix one end of each stiffening member 27 with respect to catheter adapter 24. The other end of each stiffening member 27 is fixed to catheter adapter 24 because catheter adapter 24 and stiffening members 27 are initially formed by injection molding these two elements as one piece. With this arrangement, stiffening members 27 are not dislodged from their location even under the high pressure of the injection molding process. Pins 90 also ensure that suture holes 28 are formed in the material overmolded onto stiffening members 27. See FIGS. 7 and 8.

Figure 12:
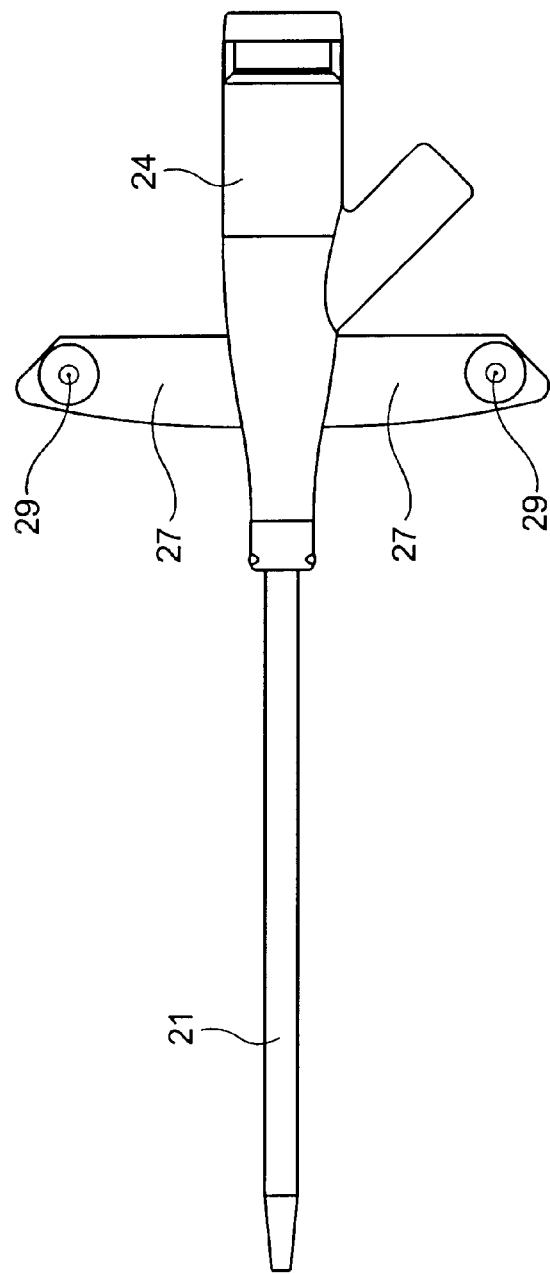
FIG. 12 is a top plan view of a partially assembled integrated catheter similar to FIG. 3 showing an alternative embodiment of the stiffening members prior to the wings being overmolded thereon.
Figure 13:
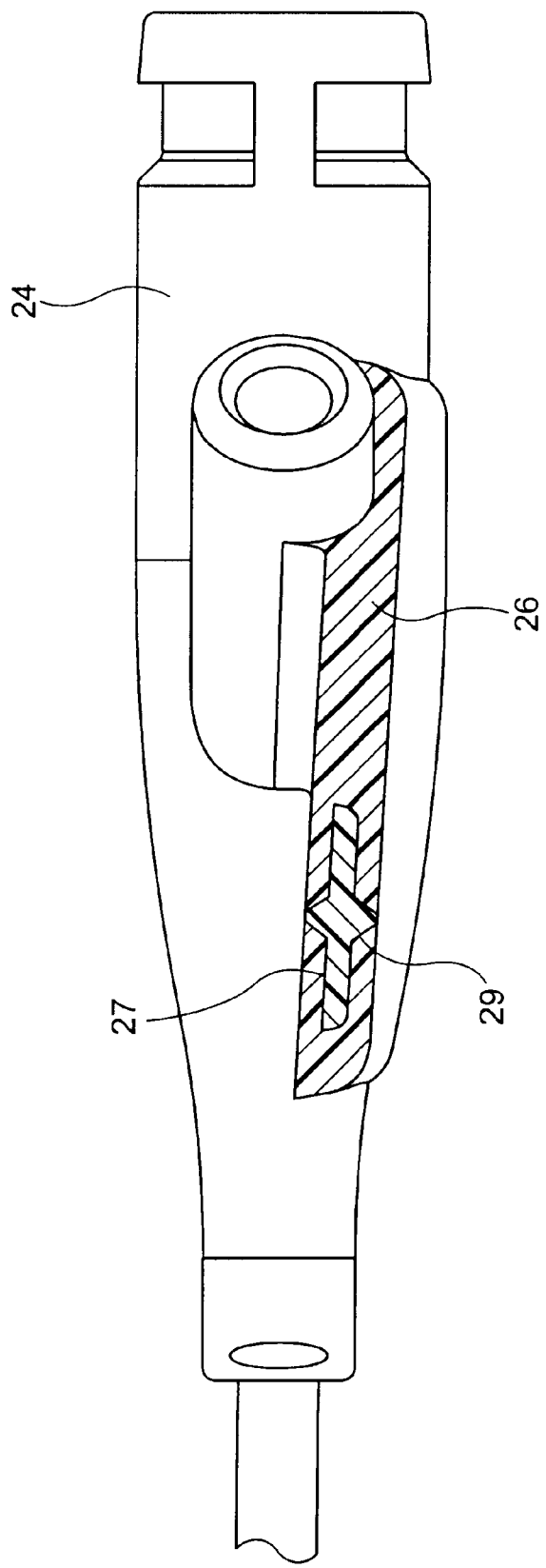
FIG. 13 is a side elevation view, partially in cross section, similar to FIG. 6 showing the alternative embodiment of the stiffening members used in an integrated catheter.

An alternative means for precisely locating each stiffening member 27 with respect to each wing 26 to be overmolded thereon is shown in FIGS. 12 and 13. Instead of suture holes 28 formed in stiffening members 27, a radially extending support 29 can be formed on stiffening member 27. At least one such support 29 should be used but preferably, each stiffening member 27 includes a pair of supports 29 such that one extends upwardly and another extends downwardly from the top and bottom respectively of each stiffening member 27. Supports 29 engage holes (not shown) formed in mold 99 to precisely locate each stiffening member 27 with respect to each wing 26.

Introducer needle assembly 30 includes introducer needle 31 having a sharp distal tip 32 defined by a bevel and a proximal end connected to a needle hub 34. Introducer needle 31 is preferably formed from stainless steel and has a longitudinal axis that is generally parallel to the longitudinal axis of catheter and introducer needle assembly 10. Introducer needle 31 may be formed with a notch adjacent to the distal end. This configuration allows blood to flow into the open distal end of introducer needle 31 and then out of the notch into the annular space between catheter 21 and introducer needle 31. If catheter 21 is at least translucent, the clinician will be able to observe blood flashback promptly upon successful venipuncture. In addition, when the blood flows into extension tube 25, if extension tube 25 is at least translucent, the clinician will also be able to observe blood flashback there. If desired and where no notch is formed in introducer needle 31, needle hub 34 can include an integrated flashback chamber having an open proximal end that is closed to fluid flow by a vented plug which allows air but not fluid to flow therethrough. Needle hub 34 may be formed from the same types of materials that are used to form catheter adapter 24. Of course, other materials could be used to form needle hub 34.

Introducer needle assembly 30 also includes a needle shield, which includes a housing defining an internal cavity therein with a proximal opening and a distal opening in communication with the internal cavity. This allows introducer needle 31 to extend longitudinally through the housing. The lock that prevents unwanted proximal and distal movement of sharp distal tip 32 of introducer needle 31 out of the distal end of the needle shield once sharp distal tip 32 has been proximally withdrawn into the needle shield can take many forms. Such a lock does not comprise this invention. The details of such a lock are described in U.S. patent application Ser. No. 09/717,148 filed Nov. 21, 2000 (P-4203P1P1P1).

Figure 9:
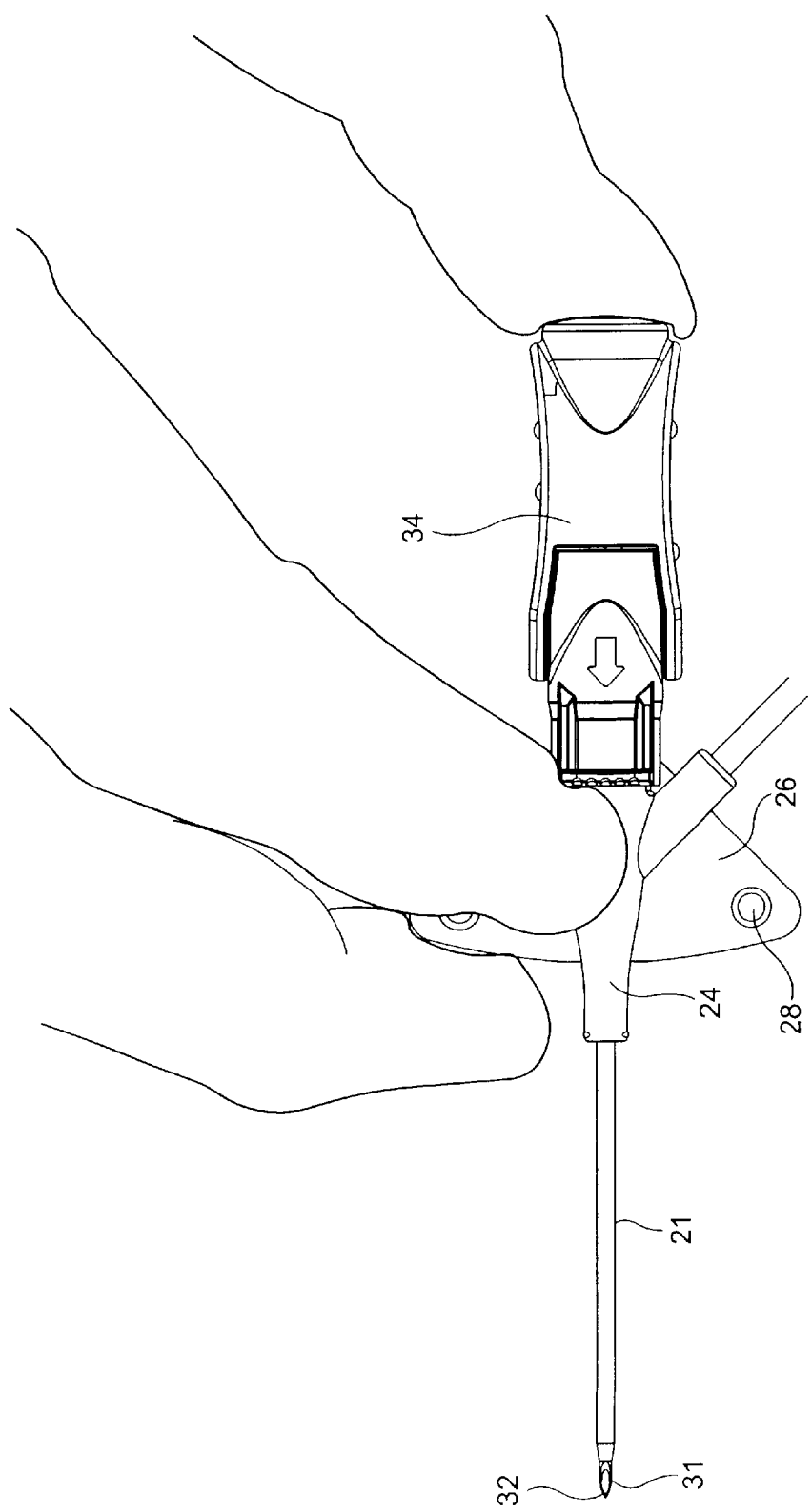
FIG. 9 is a top plan view of the integrated catheter and introducer needle assembly of FIG. 1 showing how a clinician could hold the assembly to insert the integrated catheter into a patient.
Figure 10:
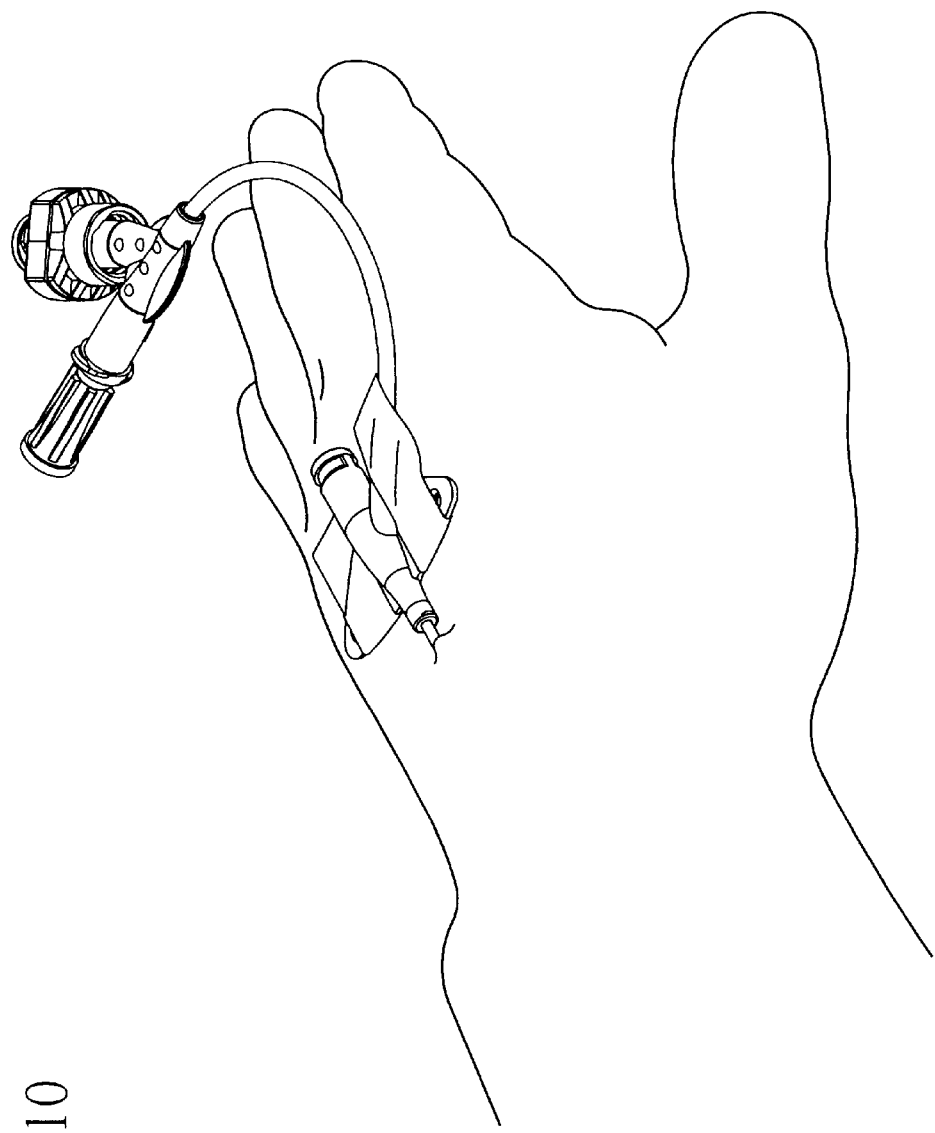
FIG. 10 is a perspective view showing the integrated catheter of FIG. 1 taped to the patient's skin.
Figure 11:
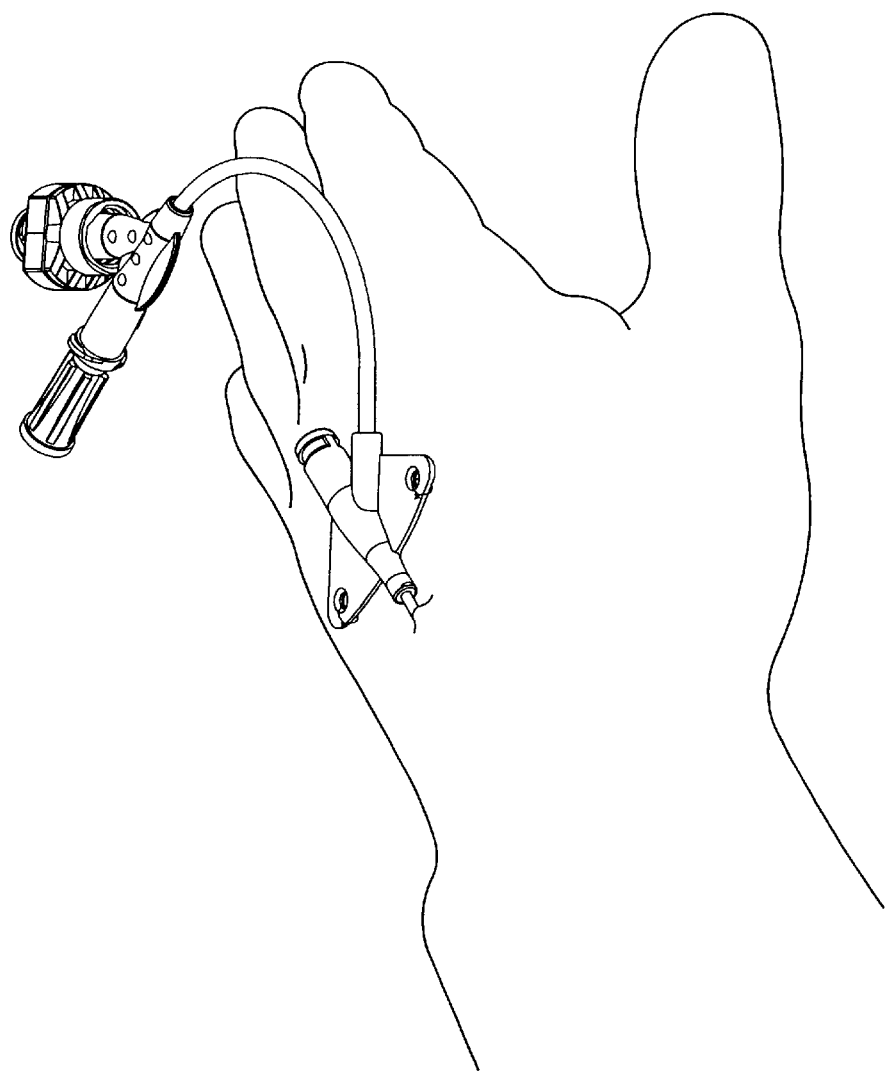
FIG. 11 is a perspective view showing the integrated catheter of FIG. 1 sutured to the patient's skin.

In order to place catheter 21 into a patient's blood vessel, the clinician grasps the integrated catheter and introducer needle assembly to substantially longitudinally align introducer needle 31 and catheter 21 with the target blood vessel. The clinician can place her fingers along the front of wings 26 as shown in FIG. 9 to stabilize and orient the assembly as needed. The bevel of sharp distal tip 32 should be facing substantially away from the skin surface during venipuncture so the distal opening to introducer needle 31 is facing away from the skin surface. The clinician inserts introducer needle 31 and catheter 21 at a shallow angle, preferably less than about 35 degrees, into the skin so that sharp distal tip 32 enters the target blood vessel. Where catheter 21, catheter adapter 24 and extension tube 25 are made from translucent material and a notch is formed in introducer needle 31, the clinician will be able to observe blood flashback along catheter 21, in catheter adapter 24 and in extension tube 25. Alternatively, where a flashback chamber is included in needle hub 34, the clinician can observe blood flashback there.

After confirming placement of introducer needle 31 and catheter 21 in the target blood vessel, the clinician advances catheter 21 distally axially along introducer needle 31 into position in the blood vessel. In certain techniques, introducer needle 31 may be partially withdrawn into catheter 21 before catheter 21 is completely advanced into position in the blood vessel. After proper placement of catheter 21 is achieved, the clinician places a finger from her other hand on the patient's skin over the blood vessel approximately over the distal end of catheter 21. By placing her finger on the patient's skin and applying sufficient pressure on the skin, the clinician thereby substantially occludes or at least minimizes blood flow through catheter 21. The clinician then withdraws introducer needle 31 completely from catheter 21 by moving needle hub 34 proximally. This movement causes introducer needle 31 to move proximally into the needle shield. Introducer needle 31 and the needle shield are removed from catheter hub 24 and disposed of according to the facility's disposal protocol. Thereafter, the clinician may then attach a fluid delivery device, a PRN, a deadender cap or some other blood monitoring device to extension tube 25 and commence the planned treatment. Alternatively, such a device can be connected to extension tube 25 prior to venipuncture. The clinician can then bend wings 26 so they match the contour of the patient's skin and suture catheter assembly 20 to the patient's skin using suture holes 28. Alternatively, the clinician can tape catheter assembly 20 to the patient's skin.

Thus, it is seen that a catheter is provided that maximizes patient comfort when the catheter is affixed to the patient's skin, that also maximizes the ability of the clinician to precisely control the catheter during venipuncture, and that balances the functional and ornamental characteristics of wings formed from soft, flexible material and wings formed from hard, rigid material. It is also seen that a method is provided that facilitates the manufacture of the catheter described herein.

We claim:

1. A catheter assembly, comprising: a translucent catheter; and a catheter adapter defining a main body portion having a translucent top portion and having at least one wing extending from a bottom portion of the catheter adapter and a stiffening member disposed in the wing, wherein the wing defines a suture hole extending through the wing and the stiffening member and wherein the stiffening member resists flexing of the wing with respect to the catheter adapter.

2. The catheter assembly of claim 1 wherein the stiffening member is formed from a first material and the wing is formed from a second material.

3. The catheter assembly of claim 2 wherein the first material is more rigid than the second material.

4. The catheter assembly of claim 1 wherein a first support extends upwardly from the stiffening member.

5. The catheter assembly of claim 4 wherein a second support extends downwardly from the stiffening member.

6. The catheter assembly of claim 1 wherein the stiffening member is formed from a first material and the wing is formed from a second material.

7. The catheter assembly of claim 6 wherein the first material is more rigid than the second material.

8. The catheter assembly of claim 1 wherein the suture hole extends through an end portion of the stiffening member that is remote from the main body portion of the catheter adapter.

9. A catheter assembly including:
   a catheter;
   a catheter adapter attached to the catheter and defining a main body portion;
   a stiffening member attached to the main body portion; and
   a flexible wing, separate from the stiffening member, enveloping the stiffening member wherein the stiffening member is permanently disposed within the flexible wing and the flexible wing is adapted to be bent to match the contour of the patient's skin.

10. The catheter assembly of claim 9 wherein the flexible wing defines a suture hole extending therethrough.

11. The catheter assembly of claim 10 wherein the suture hole extends through the stiffening member.

12. The catheter assembly of claim 11 wherein the suture hole extends through an end portion of the stiffening member that is remote from the main body portion of the catheter adapter.

13. The catheter assembly of claim 9 wherein the stiffening member is formed from a first material and the flexible wing is formed from a second material, and wherein the first material is more rigid than the second material.

14. The catheter assembly of claim 9 further comprising a support extending from the stiffening member.

15. An assembly including:

a catheter adapter defining a main body portion;

a stiffening member attached to the main body portion; and a flexible wing completely enveloping the stiffening member;

wherein the flexible wing is less rigid than the stiffening member and wherein the flexible wing is adapted to be bent to match the contour of the patient's skin.

16. The assembly of claim 15 further comprising at least one radially extending support attached to the stiffening member.

17. The assembly of claim 16 wherein the at least one radially extending support is integrally formed with the stiffening member.

18. The assembly of claim 15 in which the stiffening member is integrally formed with the main body portion of the catheter adapter.

19. A catheter assembly including:

a catheter;

a catheter adapter fixedly attached to the catheter and defining a main body portion;

a stiffening member integrally formed with the main body portion, wherein the stiffening member is made of a first material; and a flexible wing attached to the catheter adapter and completely enveloping the stiffening member;

wherein the flexible wing is separate from the stiffening member and made of a second material that is less rigid than the first material.

* * * * *